United States Patent
McCurry et al.

(10) Patent No.: US 7,383,718 B2
(45) Date of Patent: Jun. 10, 2008

(54) SINGLE STAGE FLOW MODULATOR FOR PERFORMING COMPREHENSIVE CHROMATOGRAPHY

(75) Inventors: James D McCurry, Quakertown, PA (US); John V. Seeley, Grand Blanc, MI (US)

(73) Assignee: Agilent Technologies, Inc., Santa Clara, CA (US)

( * ) Notice: Subject to any disclaimer, the term of this patent is extended or adjusted under 35 U.S.C. 154(b) by 177 days.

(21) Appl. No.: 11/358,184

(22) Filed: Feb. 21, 2006

(65) Prior Publication Data

US 2007/0193336 A1 Aug. 23, 2007

(51) Int. Cl.
*G01N 30/04* (2006.01)
(52) U.S. Cl. ............ 73/23.4; 73/23.35; 73/23.41; 95/82; 95/86; 96/101; 96/104; 96/106; 422/89
(58) Field of Classification Search ........... 73/23.35, 73/23.4, 23.41; 95/82, 86, 87; 96/101, 104, 96/105, 106; 422/89
See application file for complete search history.

(56) References Cited

U.S. PATENT DOCUMENTS 5,492,555 A * 2/1996 Strunk et al. ............ 95/86
6,966,212 B2 11/2005 Klee et al.

OTHER PUBLICATIONS

McCurry, J.D. et al., "Analysis of Trace (mg/kg) Thiophene in Benzene Using Two-Dimensional Gas Chromatography and Flame Ionization Detection", Agilent Technologies, Apr. 24, 2003, pp. 1-8.*

Blomberg, J. et al., "Practical and Theoretical Aspects of Designing a Flame-Ionization Detector/Mass Spectrometer Deans' Switch Pressure-flow Relations in Gas Chromatograph -Detector Interfaces Using Vacuum-Outlet Conditions", Journal of Chromatography A, vol. 831, 1999, pp. 257-265.*

Marriott, P.J. et al., "Multidimensional and Comprehensive Two-Dimensional Gas Chromatography", Recent Applications in Multidimensional Chromatography, Dec. 2003, pp. 2-10.*

Comprehensive Two-Dimensional High-Speed Gas Chromatography with Chemometric Analysis, Carsten A. Bruckner, Bryan J. Prazen, Robert E. Synovec, Analytical Chemistry, vol. 70, No. 14, Jul. 15, 1998, pp. 2796-2804.

Flow-switching device for comprehensive two-dimensional gas chromatography, Pedro A. Bueno Jr., John V. Seeley, Journal of Chromatography A, 1027 (2004) 3-10.

Comprehensive multi-dimensional gas chromatography, John B. Phillips, Jingzhen Xu, Journal of Chromatography A, 703 (1995) 327-334.

* cited by examiner

*Primary Examiner*—Daniel S Larkin

(57) ABSTRACT

A single stage flow modulator for performing comprehensive chromatography comprises a first chromatographic column, a valve fluidically coupled to at least two fluid conduits, wherein when in a first position, the valve directs a control flow to direct an output of the first chromatographic column to a first detector, and wherein when in a second position, the valve directs a control flow to direct a portion of an output of the first chromatographic column to a second chromatographic column, wherein the portion of the output of the first chromatographic column directed to the second chromatographic column is continuously modulated throughout a sample run.

20 Claims, 5 Drawing Sheets

SINGLE STAGE FLOW MODULATOR FOR PERFORMING COMPREHENSIVE CHROMATOGRAPHY

BACKGROUND

Gas chromatography (GC) is generally performed using one or more columns to separate a sample of material into its constituent components. In conventional comprehensive two-dimensional gas chromatography, referred to as comprehensive GC-GC or GCxGC, two columns of different selectivity are linearly coupled to provide enhanced separation of complex chemical mixtures that cannot be realized by either column alone. Examples of complex matrices include fuels (e.g., gasoline, jet fuel, kerosene, diesel fuel), oils (e.g., crude oil, lubricating oils), extracts from environmental samples (e.g., air, water, and soil), food extracts and clinical samples (e.g., blood, plasma, urine, tissue extracts).

In prior GCxGC analysis systems, a one-stage or a two-stage modulator located between the primary column and the secondary column transfers the effluent from the first column to the second column. In a two-stage modulator the first stage of the modulator collects the effluent from the primary column and the second stage of the modulator transfers, or injects the collected effluent to the secondary column. Two stage modulators are typically designed as thermal or flow-switching modulators.

A thermal two-stage modulator typically uses a cryogenic material to cool the effluent in the first stage prior to transfer to the second stage. The second stage of the modulator heats the effluent prior to injecting the effluent into the secondary column. Cooling the effluent concentrates the chromatographic peaks, which improves the analysis in the secondary column. Unfortunately, thermal two-stage modulators are complicated to design and manufacture, and require the use of a cryogenic material to cool the effluent from the primary column.

A flow-switching modulator is typically less complex than a thermal two-stage modulator and does not require a cryogenic material. However, a flow-switching two-stage modulator requires the use of complex fluid couplings that must be carefully and precisely dimensioned and scaled. These requirements lead to limitations of the GC column dimensions and require reconfiguring the components and couplings of the modulator when changing columns and/or operating conditions. Flow switching also requires higher than optimum flow rates in the secondary column(s) and places limitations on the flow ratio between the primary column and the secondary column.

In a prior one-stage modulator, a fast acting diaphragm valve transfers the effluent from the primary column to the secondary column. While a diaphragm valve modulator is relatively simple to fabricate and operate, it suffers from other limitations. For example, a diaphragm valve modulator cannot be operated at temperatures exceeding approximately 250 degrees Celsius (C). This restricts the use of such a modulator to lower boiling samples. Further, mechanical valves, such as diaphragm valves, are subject to transient, temporary pressure and flow fluctuations immediately after actuation. Depending on the dimensions of the fluid couplings in the system, this can interfere with the precise transfer of the sample from the primary column to the secondary column. Further, in such a diaphragm valve, the sample material passes through the valve body, where the sample may come into contact with active or adsorptive sites from the valve material or material used to construct the valve. These sites may contaminate the sample and skew the analysis.

Therefore, it would be desirable to have the ability to efficiently perform comprehensive two-dimensional GC analysis.

SUMMARY

According to an embodiment, a single stage flow modulator for performing comprehensive chromatography comprises a first chromatographic column, a valve fluidically coupled to at least two fluid conduits, wherein when in a first position, the valve directs a control flow to direct an output of the first chromatographic column to a first detector, and wherein when in a second position, the valve directs a control flow to direct a portion of an output of the first chromatographic column to a second chromatographic column, wherein the portion of the output of the first chromatographic column directed to the second chromatographic column is continuously modulated throughout a sample run.

Other embodiments will be discussed with reference to the figures and to the detailed description of the preferred embodiments.

BRIEF DESCRIPTION OF THE FIGURES

The invention will be described by way of example, in the description of exemplary embodiments, with particular reference to the accompanying figures.

DETAILED DESCRIPTION

While described below as used in a gas chromatograph, the single stage flow modulator can be used in any analysis application where it is desirable to efficiently perform comprehensive chromatography. For example, any chromatographic system, such as liquid chromatography (LC), capillary electrophoresis (CE) or combinations of techniques, GC-LC, LC-CE, etc., can benefit from the single stage flow modulator described herein. As used herein, the term flow is intended to include forms of mass flow, programmed mass flow, or volumetric flow and/or forms of linear velocity, such as programmed linear velocity average linear velocity, inlet, outlet, or instantaneous linear velocity through a fluid conduit.

Figure 1:
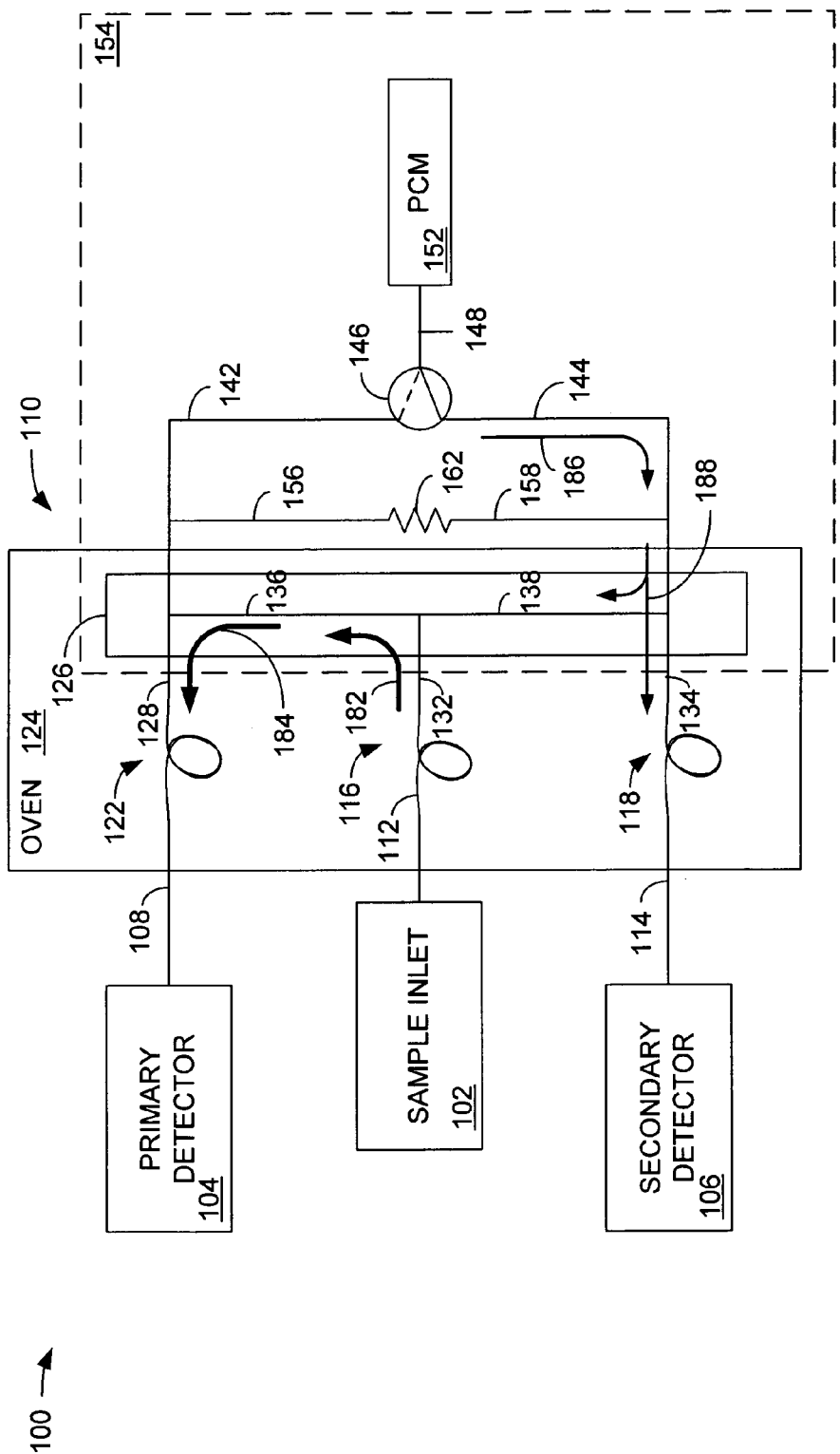
FIG. 1 is a schematic diagram conceptually illustrating a system in which a single stage flow modulator can be implemented.

FIG. 1 is a schematic diagram conceptually illustrating a system 100 in which a single stage flow modulator 110 can be implemented. The system 100 comprises a sample inlet 102 coupled to a primary column 116. In some applications, the sample inlet 102 may be coupled to the primary column via a fluid conduit 112. The primary column 116 can be selected based on the sample that is being analyzed and based on the parameters of the analysis to be performed. Similarly, the physical parameters of the fluid conduit 112 are chosen based on the analysis being performed. The output of the primary column 116 is coupled to another fluid conduit 132. The system 100 also comprises a restrictor 122 that is coupled to the output of the primary column 116 via fluid conduits 136 and 128. The output of the restrictor 122 is coupled via fluid conduit 108 to a primary detector 104. During chromatographic analysis, the primary detector 104 is used to perform analysis on the output of the primary column 116.

The system 100 further comprises a secondary column 118 that is coupled to the output of the primary column 116 via fluid conduits 132, 138 and 134. The output of the secondary column 118 is coupled via fluid conduit 114 to a secondary detector 106. The secondary detector 106 is used to perform analysis on the output of the secondary column 118.

A single stage flow modulator constructed in accordance with an embodiment of the invention is illustrated using reference numeral 110. The single stage flow modulator 110 comprises a plate 126 and what is referred to as a Deans switch 154. The plate 126 can be a substrate onto which is etched a plurality of fluid channels in accordance with that disclosed in commonly-owned U.S. Pat. No. 6,966,212, entitled "Focusing Device Based On Bonded Plate Structures." The plate 126 includes fluid conduits 128, 136, 142, 132, 138, 134 and 144. The fluid conduits formed on the plate 126 are referred to as "microfluidic channels." However, the fluid conduits need not be etched. Discrete fittings can be used to form the fluid conduits and Deans switch described above.

The Deans switch 154 comprises the plate 126, a valve 146 and a pressure control module 152. The plate 126 is coupled to the valve 146 via fluid conduits 142 and 144. As a non-limiting example, the valve 146 may be implemented using a solenoid valve. In an embodiment, at least a portion of the fluid conduit 142 and at least a portion of the fluid conduit 144 are formed on the plate 126 as microfluidic channels as described above. The pressure control module 152 is coupled to the valve 146 via fluid conduit 148. The valve 146 is controlled by a controller (not shown in FIG. 1) that uses a number of different control events, or parameters, to control the flow of fluid in the system 100. In FIG. 1, the valve 146 is shown in the "off" state.

A purge restrictor 162 is coupled to fluid conduit 142 via fluid conduit 156 and is coupled to fluid conduit 144 via fluid conduit 158. All of the fluid conduits described herein are sized based on the analysis being performed. The purge restrictor 162 prevents unintended fluid flow when the valve 146 is switched between positions, as will be described below.

In accordance with a first embodiment of the invention, when the valve 146 is in the position shown in FIG. 1, designated as the "off" position (i.e., the flow from the valve 146 is directed into fluid conduit 144 as illustrated using arrow 186), the output of the primary column 116 is directed through the fluid conduits 132 and 136 to the input of the restrictor 122 via fluid conduit 128. This flow is illustrated using arrows 182 and 184. In this manner, effluent from the primary column 116 is directed to the restrictor 122 so that normal gas chromatography can be performed. In this embodiment, the output of the restrictor 122 is directed to the primary detector 104.

The flow from the valve 146 through the fluid conduits 144, 138 and 134, as illustrated using arrow 188, forces the output of the primary column 116 to the input of the restrictor 122. As will be described below, in accordance with an embodiment of the invention, the single stage flow modulator 110 accomplishes the switching of the effluent from the primary column 116 to the secondary column 118 using single stage architecture.

However, because there is no ability to concentrate the effluent from the first column, the single stage flow modulator 110 cannot direct 100% of the effluent from the primary column 116 to the secondary column 118. A portion of the output of the primary column 116 is modulated so that it is directed to the restrictor 122, as described above.

Figure 2:
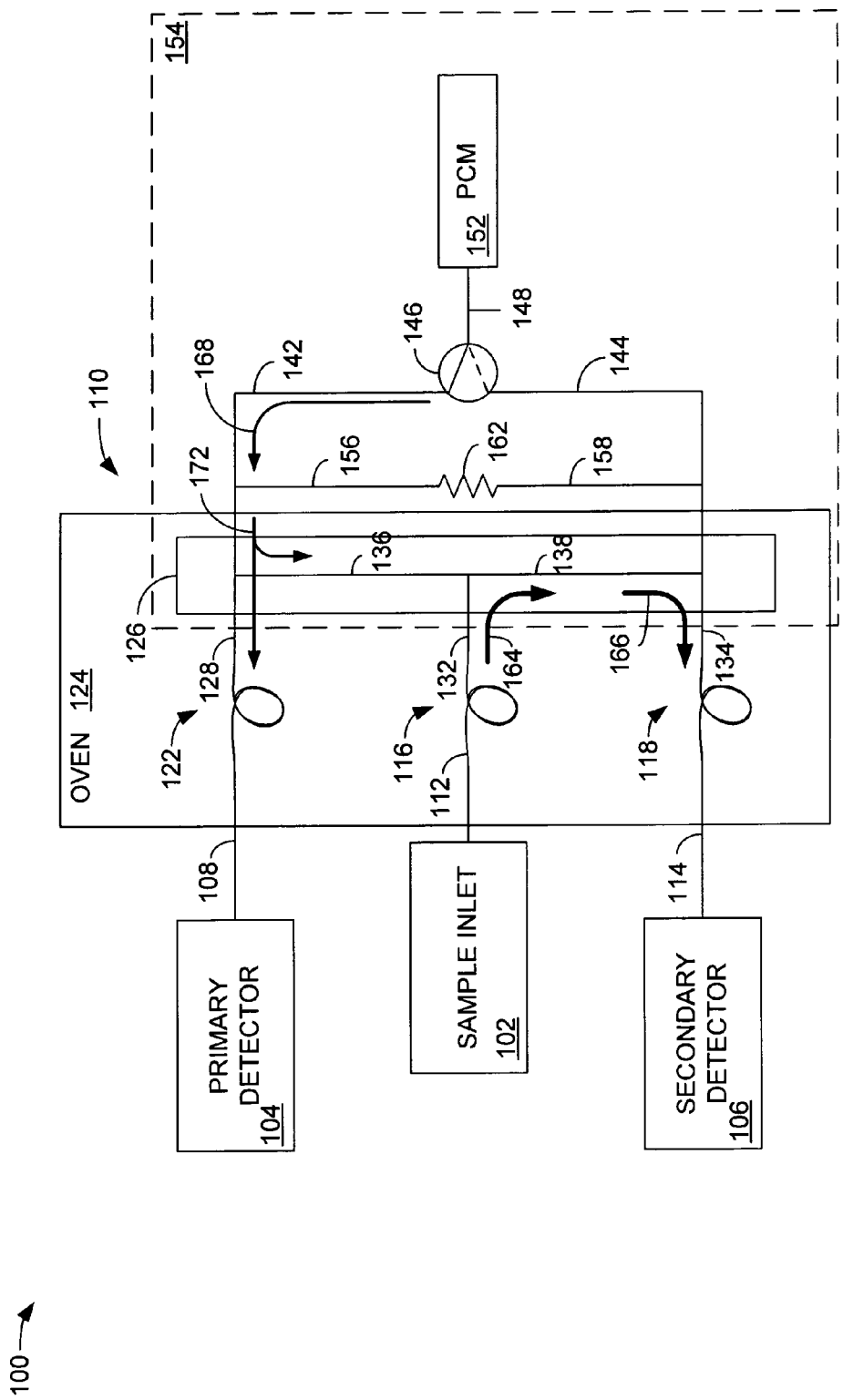
FIG. 2 is a schematic diagram conceptually illustrating the system of FIG. 1 in which the single stage flow modulator directs the effluent from the primary column to the secondary column.

FIG. 2 is a schematic diagram conceptually illustrating the system 100 of FIG. 1 in which the single stage flow modulator 110 directs the effluent from the primary column 116 to the secondary column 118.

In this embodiment, the valve 146 is switched so that its output flow is directed via fluid conduit 142, as shown using arrow 168. In this position, the flow from the valve 146 causes the output of the primary column 116 to be directed via fluid conduits 132 and 138 to the input of the secondary column 118, as shown using arrows 164 and 166. In FIG. 2, the valve 146 is shown in the "on" state.

The flow from the valve 146 through the fluid conduits 142, 136 and 128, as illustrated using arrow 172, forces the output of the primary column 116 to the input of the secondary column 118. In accordance with an embodiment of the invention, the single stage flow modulator 110 accomplishes the switching of the effluent from the primary column 116 to the secondary column 118 using a single stage topology.

In an embodiment, approximately 5% to 10% of the effluent from the primary column 116 is sampled and directed to the secondary column 118, thus allowing a simplified manner of performing comprehensive GCxGC analysis. However, percentages of the primary column effluent ranging from approximately fractions of a percent to 20% can be directed to the secondary column 118. This arrangement allows the flexibility to use different columns and physical parameters without having to reconfigure any of the fluid conduits in the system 100. In accordance with an aspect of the invention, when changing columns, only the desired flows and pressures are calculated based on the physical parameters of the columns, the restrictor and the fluid conduits in the system. This greatly simplifies the performance of comprehensive gas chromatography.

Figure 3:
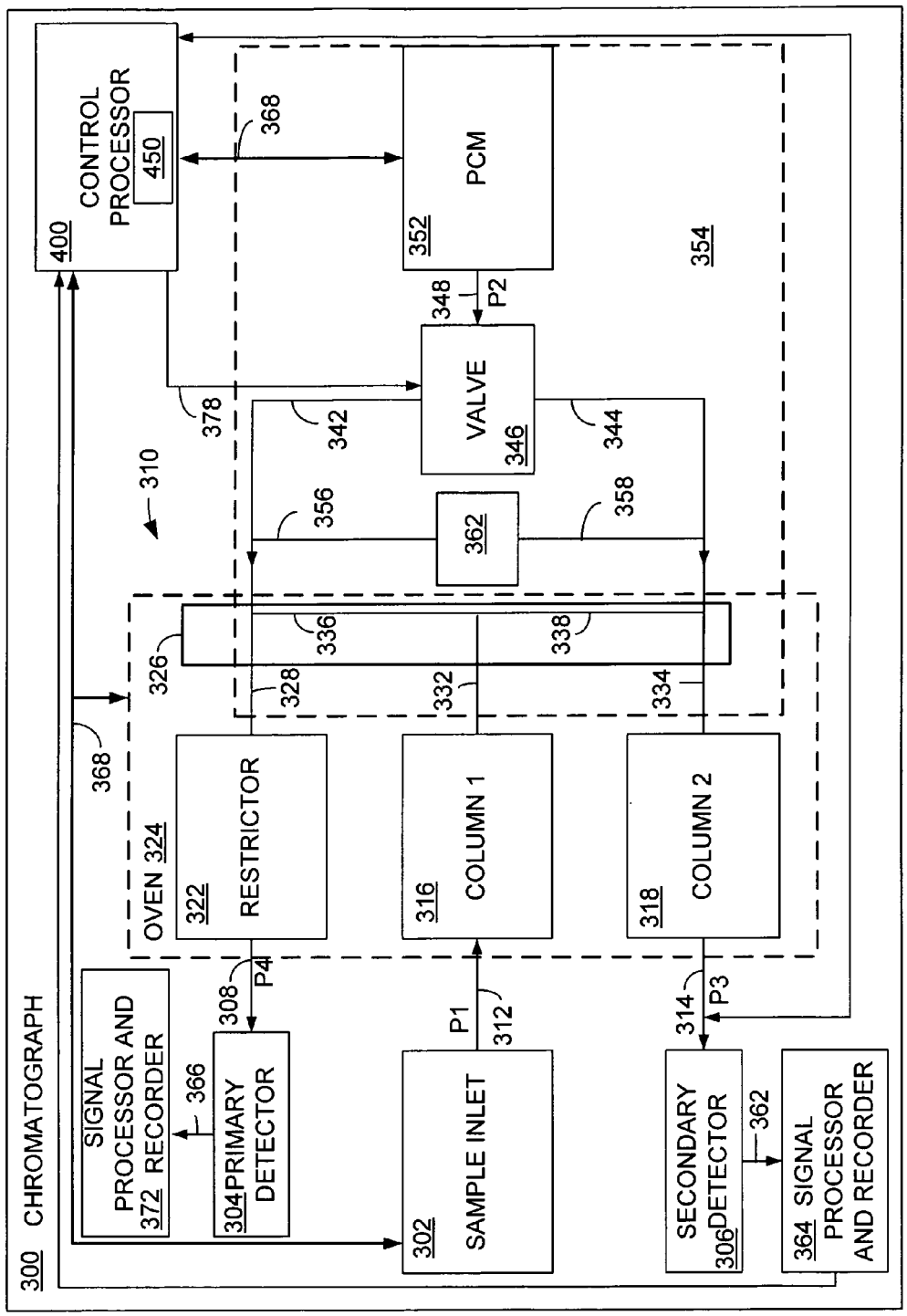
FIG. 3 is a block diagram illustrating a chromatograph including an embodiment of the single stage flow modulator.

FIG. 3 is a block diagram illustrating a chromatograph 300 including an embodiment of the single stage flow modulator. As stated above, chromatography is one example of a system in which a single stage flow modulator can be implemented. The chromatograph 300 includes many elements that are similar to the elements described in FIGS. 1 and 2. The elements in FIG. 3 that are similar to the above-described elements are denoted by the numbering convention 3XX, where XX corresponds to a similar element in FIG. 1 and FIG. 2. For example, the sample inlet 302 in FIG. 3 is similar to the sample inlet 102 of FIG. 1 and FIG. 2.

The chromatograph 300 comprises a sample inlet 302 coupled to a primary column 316 via a fluid conduit 312 having pressure P1. The primary column 316 can be selected based on the sample that is being analyzed and based on the parameters of the analysis to be performed. Similarly, the physical parameters of the fluid conduit 312 are chosen based on the analysis being performed. The output of the primary column 316 is coupled to another fluid conduit 332. The physical parameters of the fluid conduit 332 are chosen based on the analysis being performed. The chromatograph 300 also comprises a restrictor 322 that is coupled to the output of the primary column 316 via fluid conduits 332, 336 and 328. The output of the restrictor 322 is coupled via fluid conduit 308, having pressure P4, to a primary detector 304. The output of the primary detector 304 is coupled via connection 366 to a signal processor and recorder 372, which operates on the output of the primary detector 304 as known to those skilled in the art. During chromatographic analysis, the primary detector 304 is used to perform analysis on the output of the primary column 316.

The chromatograph 300 further comprises a secondary column 318 that is coupled to the output of the primary column 316 via fluid conduits 332, 338 and 334. The output of the secondary column 318 is coupled via fluid conduit 314, having pressure P3, to a secondary detector 306. The output of the secondary detector 306 is coupled via connection 362 to a signal processor and recorder 364, which operates on the output of the secondary detector 306 as known to those skilled in the art. The secondary detector 306 is used to perform analysis on the output of the secondary column 318.

One or more of the primary detector 304 and the secondary detector 306 can be implemented as a selective detector, such as a mass spectral detector, a chemiluminescent detector, or an electron capture detector, to detect and quantify trace compounds in a complex sample matrix.

A single stage flow modulator constructed in accordance with an embodiment of the invention is illustrated using reference numeral 310. The single stage flow modulator 310 comprises a plate 326 and what is referred to as a Deans switch 354. The plate 326 can be a substrate onto which is etched a plurality of fluid channels in accordance with that disclosed in commonly-owned U.S. Pat. No. 6,966,212, entitled "Focusing Device Based On Bonded Plate Structures." The plate 326 includes fluid conduits 328, 336, 342, 338, 334 and 344. The fluid conduits formed on the plate 326 are referred to as "microfluidic channels." However, the fluid conduits need not be etched. Discrete fittings can be used to form the fluid conduits and Deans switch described above.

The Deans switch 354 comprises the plate 326, a valve 346 and a pressure control module 352. The plate 326 is coupled to the valve 346 via fluid conduits 342 and 344. In an embodiment, at least a portion of the fluid conduit 342 and at least a portion of the fluid conduit 344 are formed on the plate 326 as microfluidic channels as described above. The pressure control module 352 is coupled to the valve 346 via fluid conduit 348, having pressure P2. The valve 346 is coupled to a control processor 400 via connection 378. The control processor 400 controls the operation of the valve 346. In one embodiment, the control processor 400 synchronizes the modulation of the valve 346 with the chromatographic operation being performed so that the valve 346 is synchronized with the start of the chromatographic run and with the clock (not shown) that controls the detectors 304 and 306. In this manner, the valve 346 modulates the flow from the primary column 316 to the restrictor 322 and to the secondary column 318. For example, a number of different control events, or parameters, can be used to control the operation of the valve 346 and the flow of fluid in the chromatograph 300. For example, the valve 346 will repeatedly switch from the off state (schematically shown in FIG. 1) to the on state (schematically shown in FIG. 2) at regular time intervals throughout the chromatographic analysis, thus continuously modulating the output from the primary column 316 that is directed to the secondary column 318. In some circumstances, the period of this time interval can be varied to achieve certain functions, such as solvent venting, diverting compounds that are incompatible with the secondary column 318, and heart cutting.

A purge restrictor 362 is coupled to fluid conduit 342 via fluid conduit 356 and is coupled to fluid conduit 344 via fluid conduit 358. All of the fluid conduits described herein are sized based on the analysis being performed. The purge restrictor 362 prevents unintended fluid flow when the valve 346 is switched between positions, as will be described below.

When the valve 346 is set to direct the flow from the valve 346 into fluid conduit 342 the output of the primary column 316 is directed through the fluid conduits 332 and 338 to the input of the secondary column 318 via fluid conduit 334. In this manner, effluent from the primary column 316 is directed to the secondary column 318 so that comprehensive gas chromatography can be performed. In this embodiment, the output of the secondary column 318 is directed to the secondary detector 306.

The flow from the valve 346 through the fluid conduits 342, 336 and 328, forces the output of the primary column 316 to the input of the secondary column 318. In accordance with an embodiment of the invention, the single stage flow modulator 310 accomplishes the switching of the effluent from the primary column 316 to the secondary column 318 using a single stage architecture.

However, because there is no ability to concentrate the effluent from the first column, the single stage flow modulator 310 cannot direct 100% of the effluent from the primary column 316 to the secondary column 318. A portion of the output of the primary column 316 is modulated so that it is directed to the restrictor 322, as described as above.

The single stage flow modulator 310 allows two separate data channels. The first data channel results from a one-dimensional separation of the sample using the primary column 316. In this embodiment, most of the sample (approximately 90% to 95%) is directed through the primary column 316 and analyzed using the primary detector 304. This is referred to as one-dimensional analysis. The second data channel results from the interaction of the sample on both the primary column 316 and the secondary column 318, thus providing the comprehensive GCxGC, or two-dimensional, analysis. In this manner, the single stage flow modulator provides two separate and independent analysis channels.

The first data channel also provides real-time monitoring of the separation performed in the primary column 316. This data channel can be used to optimize the modulation of the output of the primary column 316 between the restrictor 322 and the secondary column 318 based on peak widths eluting from the primary column 316.

The first data channel can also be used in combination with a selective detector, such as a mass spectral detector, a chemiluminescent detector, or an electron capture detector, to detect and quantify trace compounds in a complex sample matrix or obtain spectral information on the column effluent. Further, the higher resolution analysis data available from the second data channel (i.e., the comprehensive GCxGC analysis) can be used to provide information on possible interferences with selective detection on the first data channel. This information is useful when optimizing operation and interpreting data from a selective detector.

The single stage flow modulator 310 can be back flushed to remove high boiling components in the sample from the primary column 316, thus shortening the overall analysis time and minimizing or preventing contamination of the secondary column 318.

Further, the single stage flow modulator 310 allows two types of multidimensional GC analysis to be performed. The single stage flow modulator allows what is referred to as "heart cutting" two-dimensional analysis, in which a relatively large time segment, corresponding to a relatively large amount of effluent, of the primary column effluent is transferred to the secondary column. Typically, the "heart cut" is greater than twenty seconds and up to several minutes in duration. Once the heart cut is on the second column, the time domain for the second separation is fairly long, several minutes or greater. Typically, due to time constraints, only a few conventional heart cuts can be performed per analysis. This capability can be combined with operation as a comprehensive GCxGC modulator so that two different modes of multidimensional chromatography can be performed during the sample run. The single stage flow modulator 310 can be used in "heart cutting" mode to divert compounds that are incompatible with the secondary column 318, thus extending the service life of the secondary column 318. This capability also allows a greater choice of column combinations that are unavailable when a conventional GCxGC modulator is used. In the heart cutting method described herein, comprehensive GCxGC can be thought of as continuous heart cutting of very short duration, usually every one to ten seconds, made during the entire duration of the primary column separation. Each "heart cut" in comprehensive GCxGC completes its separation on the second column before the next "heart cut" is made. Therefore, in accordance with an embodiment of the invention, the time domain for the second separation is just a few seconds. For example, a first dimension separation, using the primary column 316, could be on the order of 800 seconds, while a second dimension separation, using the secondary column 318, could be on the order of 2.5 seconds.

The control processor 400 is coupled to the sample inlet 302, the oven 324 and the pressure control module 352 via communication bus 368 to control the functions and operation of the chromatograph 300. The control processor 400 executes flow automation software 450, which will be described in greater detail below.

Figure 4:
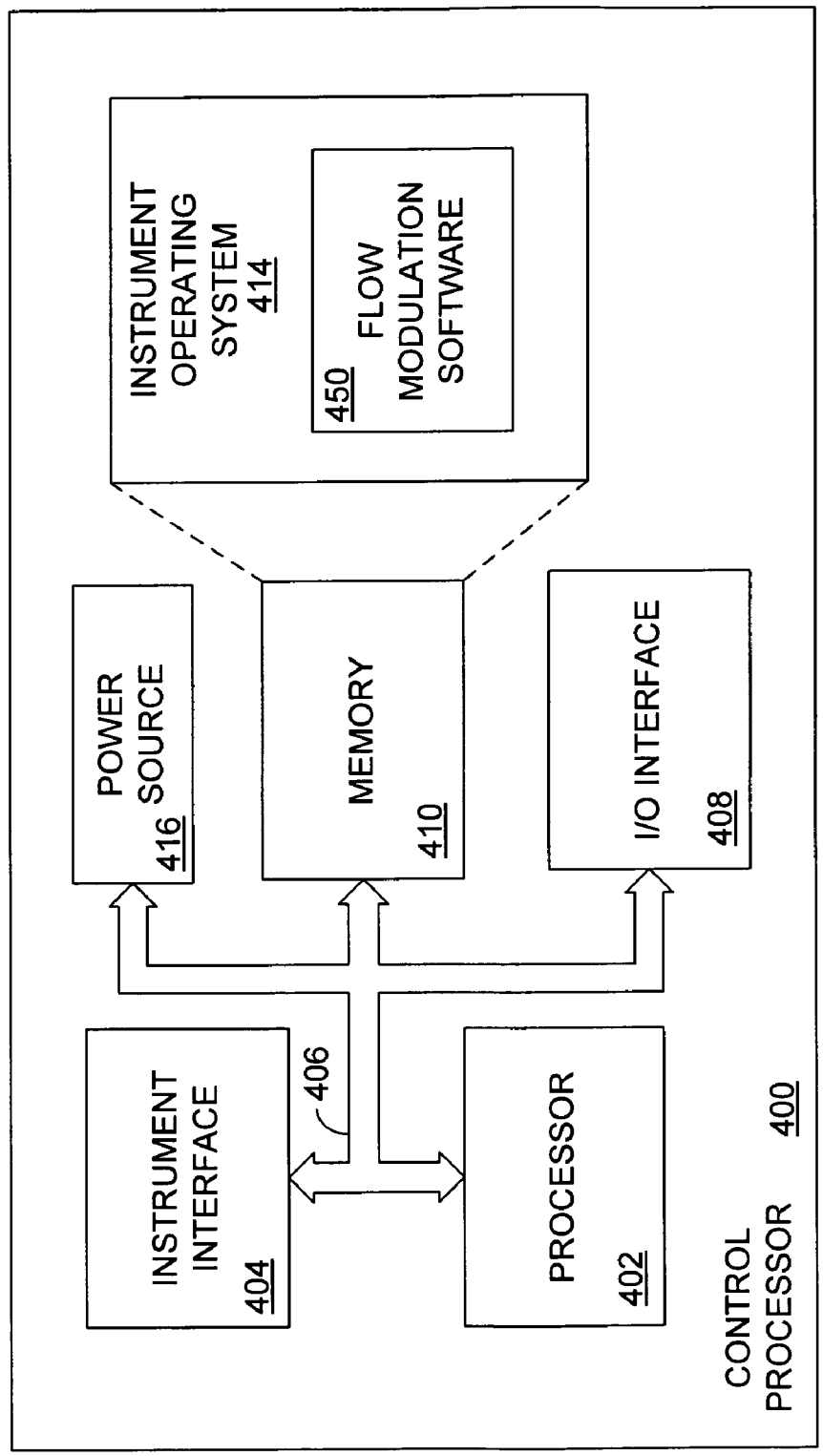
FIG. 4 is a block diagram illustrating an embodiment of the control processor of FIG. 3.

FIG. 4 is a block diagram illustrating an embodiment of the control processor 400 of FIG. 3. The control processor 400 can be any computer based control processor for controlling the operations of the chromatograph 300 of FIG. 3. Further, the control processor 400 may be internal or external to the chromatograph 300. The control of the single stage flow modulator can be implemented in hardware, software, or a combination of hardware and software. When implemented in hardware, the control of the single stage flow modulator can be implemented using specialized hardware elements and logic. When the control of the single stage flow modulator is implemented partially in software, the software portion can be used to control various operating aspects of an analysis device to control the flow of fluid through the analysis device. The software can be stored in a memory and executed by a suitable instruction execution system (microprocessor). The hardware implementation of the control of the single stage flow modulator can include any or a combination of the following technologies, which are all well known in the art: discrete electronic components, a discrete logic circuit(s) having logic gates for implementing logic functions upon data signals, an application specific integrated circuit having appropriate logic gates, a programmable gate array(s) (PGA), a field programmable gate array (FPGA), etc.

The software for the control of the single stage flow modulator comprises an ordered listing of executable instructions for implementing logical functions, and can be embodied in any computer-readable medium for use by or in connection with an instruction execution system, apparatus, or device, such as a computer-based system, processor-containing system, or other system that can fetch the instructions from the instruction execution system, apparatus, or device and execute the instructions.

In the context of this document, a "computer-readable medium" can be any means that can contain, store, communicate, propagate, or transport the program for use by or in connection with the instruction execution system, apparatus, or device. The computer readable medium can be, for example but not limited to, an electronic, magnetic, optical, electromagnetic, infrared, or semiconductor system, apparatus, device, or propagation medium. More specific examples (a non-exhaustive list) of the computer-readable medium would include the following: an electrical connection (electronic) having one or more wires, a portable computer diskette (magnetic), a random access memory (RAM), a read-only memory (ROM), an erasable programmable read-only memory (EPROM or Flash memory) (magnetic), an optical fiber (optical), and a portable compact disc read-only memory (CDROM) (optical). Note that the computer-readable medium could even be paper or another suitable medium upon which the program is printed, as the program can be electronically captured, via for instance, optical scanning of the paper or other medium, then compiled, interpreted or otherwise processed in a suitable manner if necessary, and then stored in a computer memory.

The control processor 400 comprises a processor 402, memory 410, input/output (I/O) interface 408, power source 416 and instrument interface 404 in communication via bus 406. Bus 406, although shown as a single bus, may be implemented using multiple busses connected as necessary among the elements in the control processor 400.

The processor 402 and memory 410 provide the signal timing, processing and storage functions for the control processor 400. The I/O interface generally comprises the input and output mechanisms associated with the control processor 400. For example, the I/O interface 408 may comprise a keyboard, mouse, stylus, pointer, or other input mechanisms. The output portion of the I/O interface 408 may comprise a display, printer, or other output mechanism. The instrument interface 404 comprises the hardware and software used to couple the control processor 400 to the chromatograph 300 to enable communication and control between those elements. The power source 416 may comprise a direct current (DC) or an alternating current (AC) power source.

The memory 410 comprises instrument operating system software 414 and flow modulation software 450. The instrument operating system software 414 comprises the instructions and executable code for controlling the operation of the chromatograph 300. In one example, the instrument operating system software 414 may be a proprietary operating system. The flow modulation software 450 is a separate software module that can be integrated into the instrument operating system software 414 or can be implemented independently of the instrument operating system software 414. The flow modulation software 450 can be invoked to allow a user of the chromatograph 300 to automatically and independently control multiple fluid pressures and fluid flows in the chromatograph 300. In an embodiment, the flow modulation software 450 is programmed with the physical parameters (such as length and inner diameter of a chromatographic column) of the components in an analysis device and the parameters of the carrier gas to allow a user to perform a chromatographic analysis in which a portion of the effluent of a primary column is directed to a secondary column so that comprehensive gas chromatography can be performed. Further, the flow modulation software 450 allows accurate and repeatable analysis even of certain parameters of the physical plant of the chromatograph change over time or from analysis to analysis. For example, changing one of the columns of a chromatograph can change the fluid flow in the system. The physical parameters, e.g., the length and inner diameter, of the new column can be entered into the flow modulation software 450 so that input and output pressures can be adjusted so that complex analyses can be duplicated, even if one or more components are changed.

Figure 5:
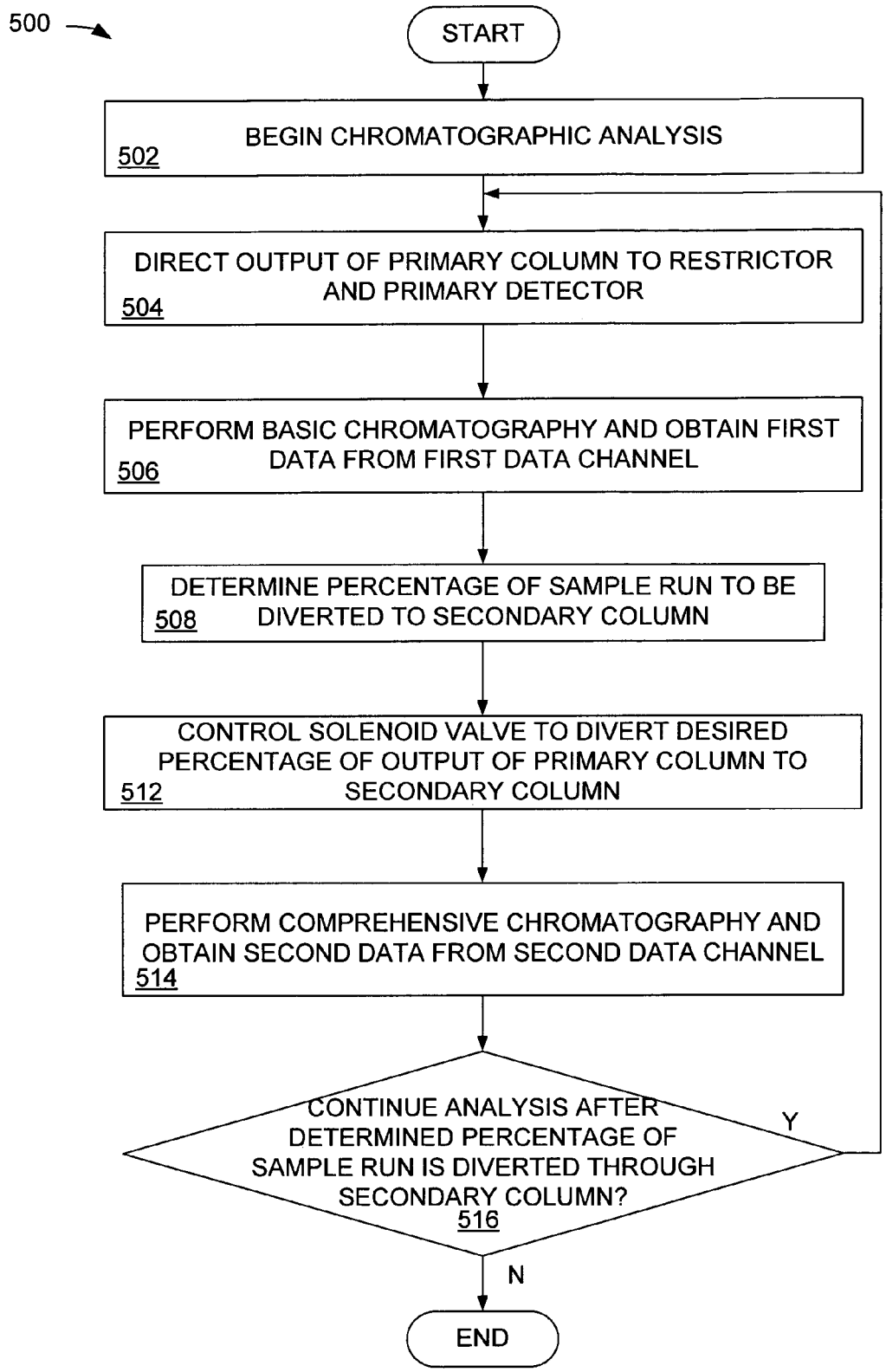
FIG. 5 is a flow chart illustrating the operation of an embodiment of the single stage flow modulator as applied to a chromatographic analysis having two columns.

FIG. 5 is a flow chart illustrating the operation of an embodiment of the single stage flow modulator as applied to a chromatographic analysis having two columns. However, the principles of the single stage flow modulator apply to other fluid systems in which it is desirable to perform comprehensive chromatography using a single stage flow modulator. The blocks in the flowchart can be performed in the order shown or out of the order shown, or can be performed in parallel. In block 502, a chromatographic analysis is begun. In block 504, the output of a primary column is directed to a restrictor and to a primary detector. In block 506, basic, single channel, chromatography is performed on the sample by the primary column and the primary detector. In block 508, the percentage of primary column effluent that is to be directed to a secondary column for comprehensive chromatographic analysis is determined. In one example, approximately 5% to 10% of the effluent from a primary column may be directed to a secondary column. In this manner, a chromatographic separation performed on the second chromatographic column can be fine tuned.

In block 512, the control processor 400 controls the valve 346 to divert the desired amount of effluent from the primary column to the secondary column. In one example, approximately 5% to 10% of the effluent is directed from the primary column 316 to the secondary column 318. In block 514, comprehensive chromatography is performed on the effluent diverted to the secondary column. The output of the secondary column and secondary detector comprises a portion of the sample that has undergone analysis by the primary column and the secondary column, and therefore provides two channels of data on the sample. Selectively operating the single stage flow modulator 310 to direct only a portion of the effluent from the primary column 316 to the secondary column 318 simplifies the overall data analysis and reduces the size of the data files that are output from the primary detector 304 and the secondary detector 306. In block 516, it is determined whether to continue the analysis after the determined percentage of sample from the primary column is diverted to the secondary column for analysis. If it is determined in block 516 that the analysis is to continue, then the process returns to block 504. If it is determined in block 516 that the analysis is complete, then the process ends. Further, modulation time, which refers to the amount of primary column effluent that is diverted to the secondary column, can be varied during the analysis to fine tune the separation performed on the secondary column 318.

The foregoing detailed description has been given for understanding exemplary implementations of the invention and no unnecessary limitations should be understood therefrom as modifications will be obvious to those skilled in the art without departing from the scope of the appended claims and their equivalents. Other devices may use the single stage flow modulator described herein.

What is claimed is:

1. A single stage flow modulator for performing comprehensive chromatography, comprising:

a first chromatographic column; and a valve fluidically coupled to at least two fluid conduits, wherein when in a first position, the valve directs a control flow to direct an output of the first chromatographic column to a first detector; and wherein when in a second position, the valve directs a control flow to direct a portion of an output of the first chromatographic column to a second chromatographic column, wherein the valve is isolated from the portion of the output of the first chromatographic column and from an input of the second chromatographic column and uses pressure to direct the control flow, wherein the portion of the output of the first chromatographic column directed to the second chromatographic column is directly transferred from the first chromatographic column to the second chromatographic column and is continuously modulated throughout a sample run to perform continuous heart cutting throughout the sample run resulting in each peak eluting from the first chromatographic column having at least some portion transferred to the second chromatographic column.

2. The flow modulator of claim 1, wherein the valve and the at least two fluid conduits are part of a Deans switch.

3. The flow modulator of claim 2, further comprising:

a first data channel resulting from a one-dimensional separation of a sample using the first chromatographic column; and a second data channel resulting from an interaction of the sample on the first chromatographic column and the second chromatographic column, thus providing comprehensive chromatography, wherein the portion of the output of the first chromatographic column that is diverted to the second chromatographic column is approximately 5% to 10% of the output of the first chromatographic column.

4. The flow modulator of claim 3, wherein a portion of the sample is directed through the first chromatographic column and analyzed using a primary detector.

5. The flow modulator of claim 4, wherein the first data channel further comprises a selective detector to perform analysis chosen from detecting and quantifying trace compounds in a complex sample and obtaining spectral data of compounds eluting from the first chromatographic column.

6. The flow modulator of claim 3, wherein, the single stage flow modulator provides two separate and independent analysis channels.

7. The flow modulator of claim 6, wherein the single stage flow modulator is selectively operated to direct only a portion of an output of the first chromatographic column to the second chromatographic column so that a chromatographic separation performed on the second chromatographic column can be fine tuned.

8. The flow modulator of claim 6, wherein the single stage flow modulator performs heart cutting two-dimensional chromatography.

9. A method for performing comprehensive chromatography, comprising:

directing an output of a primary chromatographic column to a restrictor and a primary detector;

performing chromatographic analysis using the primary column;

determining an amount of effluent from the primary column to direct to a secondary column;

controlling a valve to direct the desired amount of effluent from the primary column to the secondary column using a single stage flow modulator using pressure to direct the control flow; and performing comprehensive chromatography using the secondary column, wherein the portion of the output of the primary column directed to the secondary column is directly transferred from the primary column to the secondary column and is continuously modulated throughout a sample run to perform continuous heart cutting throughout the sample run resulting in each peak eluting from the primary column having at least some portion transferred to the secondary column.

10. The method of claim 9, wherein the valve and the at least two fluid conduits are part of a Deans switch.

11. The method of claim 10, further comprising:

forming a first data channel resulting from a one-dimensional separation of a sample using the primary column; and forming a second data channel resulting from an interaction of the sample on the primary column and the secondary column, thus providing comprehensive chromatography, wherein the portion of the output of the primary column that is diverted to the secondary column is approximately 5% to 10% of the output of the primary column.

12. The method of claim 11, further comprising:

directing a portion of the sample through the primary column; and analyzing the portion of the sample using a primary detector.

13. The method of claim 12, wherein the first data channel further comprises analysis chosen from detecting and quantifying trace compounds in a complex sample and obtaining spectral data of the eluting compounds.

14. The method of claim 11, wherein the single stage flow modulator provides two separate and independent analysis channels.

15. The method of claim 14, further comprising selectively operating the single stage flow modulator to direct only a portion of an output of the primary column to the secondary column so that a chromatographic separation performed on the secondary column can be fine tuned.

16. The method of claim 14, further comprising performing heart cutting two-dimensional chromatography.

17. A chromatograph, comprising:

a first chromatographic column; and a valve fluidically coupled to at least two fluid conduits, the at least two fluid conduits, wherein when in a first position, the valve directs a control flow to direct an output of the first chromatographic column to a first detector; and wherein when in a second position, the valve directs a control flow to direct a portion of an output of the first chromatographic column directly to a second chromatographic column, wherein the valve is isolated from the portion of the output of the first chromatographic column and from an input of the second chromatographic column and uses pressure to direct the control flow, wherein the valve continuously modulates the portion of the output of the first chromatographic column directed to the second chromatographic column throughout a sample run to perform continuous heart cutting throughout the sample run resulting in each peak eluting from the first chromatographic column having at least some portion transferred to the second chromatographic column.

18. The chromatograph of claim 17, wherein the valve and the at least two fluid conduits are part of a Deans switch.

19. The chromatograph of claim 18, further comprising:

a first data channel resulting from a one-dimensional separation of a sample using the first chromatographic column; and a second data channel resulting from an interaction of the sample on the first chromatographic column and the second chromatographic column, thus providing comprehensive chromatography, wherein the portion of the output of the first chromatographic column that is diverted to the second chromatographic column is approximately 5% to 10% of the output of the first chromatographic column.

20. The chromatograph of claim 19, wherein the first data channel and the second data channel are two separate and independent analysis channels.

* * * * *